(12) United States Patent
Strutz et al.

(10) Patent No.: US 6,549,814 B1
(45) Date of Patent: Apr. 15, 2003

(54) BLADE ELECTRODE ARRAY FOR INSERTION UNDER SOFT TISSUE OF LATERAL WALL OF COCHLEA

(75) Inventors: Juergen Strutz, Maximilian-Aschenauer-Str. 14, D-93059 Regensburg (DE); Janusz A. Kuzma, Englewood, CO (US)

(73) Assignees: Juergen Strutz, Regensburg (DE); Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 09/876,882

(22) Filed: Jun. 7, 2001

Related U.S. Application Data (60) Provisional application No. 60/261,353, filed on Jan. 12, 2001, and provisional application No. 60/210,375, filed on Jun. 9, 2000.

(51) Int. Cl.⁷ .................................................. A61N 1/05
(52) U.S. Cl. ......................................... 607/137; 607/57
(58) Field of Search ........................ 607/116, 133–138, 607/152–156, 55, 56; 600/372–381

(56) References Cited

U.S. PATENT DOCUMENTS

| | | | |
|---|---|---|---|
| 5,545,219 A | 8/1996 | Kuzma | 623/10 |
| 5,649,970 A | 7/1997 | Loeb et al. | 607/57 |
| 6,038,485 A | * 3/2000 | Axelgaard | |
| 6,074,422 A | 6/2000 | Berrang et al. | 623/10 |
| 6,129,753 A | 10/2000 | Kuzma | 607/137 |
| 6,151,526 A | 11/2000 | Tziviskos | 607/137 |
| 6,163,729 A | 12/2000 | Kuzma | 607/137 |
| 6,304,787 B1 | 10/2001 | Kuzma et al. | 607/137 |

FOREIGN PATENT DOCUMENTS

| | | |
|---|---|---|
| WO | 9906108 | 11/1999 |
| WO | 0069512 | 11/2000 |
| WO | 0069513 | 11/2000 |

\* cited by examiner

*Primary Examiner*—Scott M. Getzow
(74) *Attorney, Agent, or Firm*—Bryant R. Gold (57) ABSTRACT

A cochlear electrode array is adapted for use with a hybrid hearing aid system. The cochlear electrode array has a carrier on which spaced-apart electrode contacts are carried, and in one embodiment is formed in the shape of a blade, being flat in one direction and thin in another direction. In another embodiment, side fins extend out from opposing sides of the carrier on which the electrode contacts are carried. The blade electrode array, or electrode array with side fins, is adapted for minimally-invasive insertion into the inner ear. More particularly, the blade or finned electrode is designed to be inserted through a soft cochleostomy so as to reside between the spiral ligament membrane and the cochlear bony tissue along a lateral side of the cochlea, near the basal end of the cochlea. As such, the blade electrode does not penetrate into the scala tympani or other ducts of the cochlea, and the cochlea remains free to perform its normal hearing functions to the extent that such normal hearing functions can be performed.

14 Claims, 7 Drawing Sheets

BLADE ELECTRODE ARRAY FOR INSERTION UNDER SOFT TISSUE OF LATERAL WALL OF COCHLEA

This application claims the benefit of U.S. Provisional Application Serial No. 60/210,375, filed Jun. 9, 2000; and U.S. Provisional Application Serial No. 60/261,353, filed Jan. 12, 2001; both of which applications are incorporated herein by reference.

BACKGROUND OF THE INVENTION

The present invention relates to implantable electrode arrays, and more particularly to an implantable electrode array configured for implantation under the soft tissue or spiral ligament on the lateral wall of a human cochlea. Such electrode array is best suited for use with a hybrid cochlear stimulator of the type described in applicant's international patent application, filed May 12, 2000, as Serial No. PCT/US00/13122, and published as International Publication WO 00/69512 on Nov. 23, 2000, entitled "Hybrid Implantable Cochlear Stimulation Hearing Aid System", which publication is incorporated herein by reference. In general, a hybrid cochlear stimulation system provides electrical stimulation only to the basal end of the cochlea to stimulate nerves, e.g., ganglion cells, hair cells, or other nerve cells, responsible for sensing higher-frequency sounds, and relies on normal hearing processes (activation of hair cells through fluid motion within the cochlea), which may occur with or without the assistance of a conventional or a custom hearing aid, to sense middle-to-lower frequency sounds.

Hearing loss is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells. Some types of conductive hearing loss are also amenable to alleviation by surgical procedures.

Sensorineural hearing loss, on the other hand, results due to the absence or the destruction of the hair cells in the cochlea which are needed to transduce acoustic signals into auditory nerve impulses. Persons who suffer from sensorineural hearing loss are unable to derive any benefit from conventional hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sounds.

To overcome sensorineural deafness, there have been developed numerous cochlear implant systems—or cochlear prosthesis—which seek to bypass the hair cells in the cochlea by presenting electrical stimuli directly to the ganglia of the auditory nerve located adjacent the modiolar wall of the cochlea. When triggered, the ganglia, also referred to as ganglion cells, send nerve impulses to the brain via the auditory nerve, leading to the perception of sound in the brain, and an at least partial restoration of hearing function. The common denominator in such cochlear prosthesis systems has been the implantation into the cochlea of electrodes which are responsive to a suitable external source of electrical stimuli and which are intended to transmit those stimuli to the ganglion cells, and thereby to the auditory nerve fibers.

It is estimated that a large segment of the hearing-impaired population exhibit sensorineural hearing loss relative to high frequency sounds, but maintain the ability to transduce middle-to-lower frequency sounds through functioning hair cells. For this segment of the population, there is thus a need for a "hybrid" cochlear stimulation system that electrically stimulates only the cells and nerves responsible for sensing higher frequency sounds, while allowing the normal hearing process to function for the purpose of sensing lower frequency sounds.

A cochlear prosthesis operates by direct electrical stimulation of the auditory nerve cells, bypassing the defective cochlear hair cells that normally transduce acoustic energy into electrical activity in such nerve cells. Because the ganglion or other cells, e.g., hair cells, responsible for sensing higher frequency sounds are all generally located in or near the basal end of the cochlea (the end of the cochlea nearest the round window membrane), a hybrid cochlear stimulation system thus requires an electrode array that can be inserted within the cochlea a sufficient depth to be near such cells, but which also does not block or significantly interfere with the normal functioning of the cochlea for hair cells located deeper within the cochlea. A preferred electrode array for use with such a hybrid cochlear stimulation system would be inserted into or near the cochlea in such a way so as not to interfere with the normal functioning of the cochlea. No such electrode array, to applicants' knowledge, currently exists.

SUMMARY OF THE INVENTION

The present invention addresses the above and other needs by providing a cochlear electrode array suitable for use with a hybrid cochlear stimulation system. In one embodiment, the cochlear electrode array comprises a relatively thin blade electrode array that is inserted underneath the spiral ligament, or soft tissue, at the lateral wall of the cochlea, without actually penetrating into any of the three main ducts that make up the cochlea: the scala tympani, the scala vestibule, or the cochlear duct.

In accordance with one aspect of the invention, the blade electrode provided by the invention is implanted into the cochlea through a "soft cochleostomy" operation. A soft cochleostomy operation is one wherein a hole is drilled into but not all the way through the bony tissue adjacent the round window. Hence, no penetration occurs into the cochlea ducts, including the scala tympani, the scala vestibule, and the cochlear duct, and all such ducts remain intact to perform their normal function.

Once a soft cochleostomy hole has been drilled, the blade of a suitable surgical instrument, or a similar tool, is inserted into the drilled hole and is used to delaminate the spiral ligament membrane from the bony tissue located at the lateral wall of the cochlea. The blade electrode of the invention is then slid into the opening created by the tissue delamination to a desired depth. The desired depth will typically be a relatively short distance, e.g., 6–12 mm. However, for some applications, the blade electrode may be inserted sufficiently deep so as to make up to a 180° turn through the cochlea.

In accordance with another aspect of the invention, the blade electrode array incorporates thin lips or side fins that extend beyond the body of the carrier of the electrode itself. Such side fins are used to fix the electrode in a groove in the bony recess prepared to hold the electrode.

In accordance with yet an additional aspect of the invention, used in an alternative embodiment thereof, the blade electrode carries one or more mechanical transducers that convert electrical current to mechanical energy, which mechanical energy is then readily coupled directly to the fluid within the cochlea, thereby assisting or aiding the triggering of hair cells that line the inside of the cochlea.

In accordance with yet another aspect of the invention, the blade electrode is inserted under the spiral ligament membrane at the lateral wall of the cochlea and is selectively energized in order to treat tinnitus.

It is a feature of the present invention to provide an electrode array for stimulating nerves and cells of the inner ear, e.g., the cochlea, without interfering with the normal operation of the inner ear, thereby allowing the selective activation of such electrode array to supplement the normal hearing processes that occur within the inner ear.

It is another feature of the invention to provide a method of inserting an electrode array into the inner ear without penetrating into the scala tympani or scala vestibuli of the cochlea, thereby permitting the cochlea to perform its normal hearing function in a minimally-invasive manner.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components or elements throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The present invention is directed to a cochlear electrode array that does not interfere with the normal functioning of the inner ear. One application for the present invention is for use with a hybrid cochlear stimulation system. Another application for the present invention is for use to supplement the normal hearing processes. Yet another application is for use of the electrode array, inserted under the spiral ligament membrane at the lateral wall of the cochlea, is to selectively energize the electrodes of the array in order to treat tinnitus.

In one embodiment, the cochlear electrode array of the present invention comprises a relatively thin blade electrode array that is inserted underneath the spiral ligament, or soft tissue, at the lateral wall of the cochlea, without actually penetrating into any of the three main ducts that make up the cochlea: the scala tympani, the scala vestibule, or the cochlear duct. The blade electrode is typically implanted into the cochlea through a "soft cochleostomy" operation. A soft cochleostomy operation is one wherein a hole is drilled into but not all the way through the bony tissue adjacent the round window. Hence, no penetration occurs into the cochlea ducts, including the scala tympani, the scala vestibuli, and the cochlear duct, and all such ducts remain intact to perform their normal function.

Once a soft cochleostomy hole has been drilled, the blade of a suitable surgical instrument, or a similar tool, is inserted into the drilled hole and is used to delaminate the spiral ligament membrane from the bony tissue located at the lateral wall of the cochlea. The blade electrode of the invention is then slid into the opening created by the tissue delamination to a desired depth. The desired depth will typically be a relatively short distance, e.g., 6–12 mm. However, for some applications, the blade electrode may be inserted sufficiently deep so as to make up to a 180° turn through the cochlea.

In another embodiment, the blade electrode array incorporates thin lips or side fins that extend beyond the body of the carrier of the electrode itself. Such side fins are used to fix the electrode in a groove in the bony recess prepared to hold the electrode.

In yet an alternative embodiment, the blade electrode carries one or more mechanical transducers that convert electrical current to mechanical energy, which mechanical energy is then readily coupled directly to the fluid within the cochlea, thereby assisting or aiding the triggering of hair cells that line the inside of the cochlea.

Figure 1:
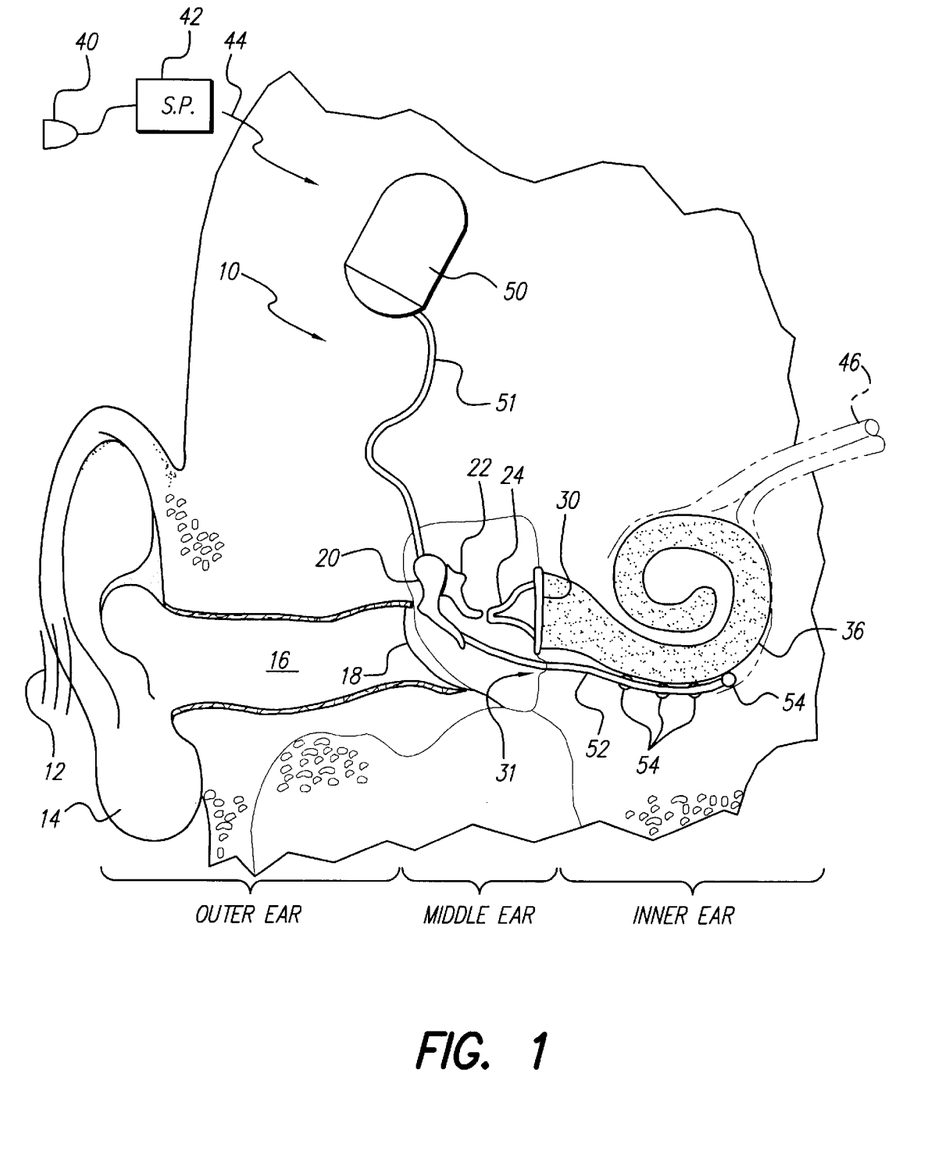
FIG. 1 is a functional schematic diagram of the ear, showing the manner in which an implantable cochlear stimulator and short cochlear electrode placed adjacent the basal region of the cochlea may be used to practice the invention in accordance with one embodiment thereof.

Turning first to FIG. 1, one embodiment of a representative hybrid cochlear stimulation system is illustrated. Such embodiment relies upon an implantable cochlear stimulator (ICS) 50 to provide direct electrical stimulation of the nerve cells located at the basal end of the cochlea, to thereby enhance the hearing of high frequency sounds; and relies upon the patient's normal hearing processes, e.g., the patient's residual low and mid frequency hearing, to sense low-to-mid frequency sounds.

The major relevant components of the outer, middle and inner ear are illustrated in FIG. 1. To better understand the present invention, it will first be helpful to briefly review the normal operation of a fully functional ear. Thus, as seen in FIG. 1, the outer ear includes the auricle 14 and the ear canal 16. An acoustic pressure wave, or sound wave, represented in FIG. 1 by the short parallel lines 12, is collected by the auricle 14 and funneled into the ear canal 16. At the end of the ear cannel 16 is the "ear drum" 18, or in medical terms, the tympanic membrane 18. In a person who is not significantly hearing impaired, the received acoustic wave 12 causes the tympanic membrane 18 to vibrate, which vibration is coupled through three tiny bones, known as the ossicles, comprising the malleus ("hammer") 20, the incus ("anvil") 22 and the stapes ("stirrup") 24, to the fenestra 30.

In anatomical terms, the fenestra comprises an opening resembling a window. The fenestra ovalis, or oval window, is the opening between the middle ear and the scala vestibule of the inner ear. It is closed by a membrane to which the stapes is attached. The fenestra rotunda, or round window, is the opening between the scala tympani of the cochlea and the middle ear. The round window is also closed by a membrane, which for purposes of the present application, may be referred to as the round window membrane. For purposes of the functional schematic diagram shown in FIG. 1, the function of both the oval window and round window is represented by the single membrane 30. In subsequent figures, only the round window is shown, and is represented by a membrane 32.

The bones of the middle ear serve to filter and amplify the perceived acoustic wave 12, causing the fenestra membrane 30 to articulate, or vibrate, in response to the acoustic wave 12. Vibration of the membrane 30 sets up waves of fluid motion within the fluid contained within the snail-shaped cochlea 36. Such fluid motion, in turn, activates tiny hair cells (not shown in FIG. 1) that line the inside of the cochlea 36. Activation of the hair cells causes appropriate nerve impulses to be transferred through the spiral ganglion cells and auditory nerve 46 to the brain, where they are perceived as sound.

The spiral ganglion and other cells responsible for the perception of high frequency sounds are generally located at the basal end of the cochlea 36, i.e., that end of the cochlea closest to the membrane 30. For those individuals who suffer from high frequency hearing loss, the hair cells in the basal region of the cochlea are ineffective or otherwise damaged to the point where it is usually not possible to activate them. Hence, in accordance with the present invention, an implantable cochlear stimulator (ICS) 50 may be implanted near the ear, and a short cochlear electrode array 52, having a plurality of spaced apart electrodes 54 thereon, is inserted into the cochlea 36 through a soft cochleostomy 31, adjacent the round window, as explained in more detail below. A short cable or lead 51 electrically connects the electrode array 52 to the ICS 50. (It is noted that while the lead 51 is shown passing through the "middle ear" in the functional diagram of FIG. 1, in practice the lead 51 is usually tunneled through tissue that bypasses or goes around the middle ear so as not to interfere in any way with the operation of the ossicles within the middle ear.)

The ICS 50 is coupled to a microphone, e.g., an external microphone 40 (although an internal, i.e., implanted, microphone could also be used) that senses sound. The microphone signals are amplified and processed by a suitable speech processor (SP) 42, which SP may also be external or implanted. The speech processor generates appropriate control signals that are coupled to the ICS 50. Such coupling may occur through various means, as are known in the art, but is usually achieved through an inductive coupling link, represented by the arrow 44, with an external head piece, connected to the speech processor 42. Such link also provides a way for power to be coupled into the implanted ICS 50. However, it is also possible for the processor and power source to be implanted, either as an integral part of the ICS 50 or in a separate housing coupled to the ICS. (See, e.g., International Publication No. WO 99/06108, published February 11, 1999, incorporated herein by reference.)

In operation, the speech processor 42 functions as a signal processing means for processing the electrical signals received from the microphone 40 and for generating high-frequency control signals therefrom representative of the higher frequency content of the sensed acoustic sounds. These control signals are then coupled to the ICS 50 through the link 44. The ICS 50 has means responsive to the high-frequency control signals for selectively generating electrical stimuli and applying the electrical stimuli to the electrode 52. In this manner, the basal region of the scala tympani 62 (see FIG. 2) of the cochlea 36 is stimulated with electrical stimuli representative of the higher-frequency content of the sensed acoustic sounds.

In accordance with the embodiment of the invention depicted in FIG. 1, the sounds sensed by the microphone 40 are processed and filtered to separate out the high frequency sounds. These high frequency sounds are then converted to appropriate electrical stimuli that are selectively applied to the electrode contacts 54 of the electrode array 52 positioned in the basal region of the cochlea. Such electrical stimuli bypass the defective hair cells in the basal region of the cochlea and directly activate the appropriate nerves within the of the spiral ganglion or elsewhere, causing nerve impulses to be transferred to the brain, where they may be perceived as high frequency sounds.

Significantly, the other hair cells in the cochlea, i.e., those in the apical and mid regions of the scala tympani 62, as well as within other ducts and locations of the cochlea, retain their functionality. That is, these hair cells are able to sense the fluid waves set up by vibrations of the oval window membrane and/or round window membrane corresponding to low-to-mid frequency sounds. Hence, the patient (or user of the hybrid system shown in FIG. 1) primarily senses high frequency sounds through the ICS portion of the system, and primarily senses mid-to-lower frequency sounds through the normal hearing processes of the ear.

Advantageously, as will be evident from the description that follows, the electrode array 52 does not penetrate into the scala tympani 62 or the scala vestibuli 64 of the cochlea 36. Hence, these ducts within the cochlea retain their full functionality, and the patient, or user of the hybrid system, is able to utilize his or her normal hearing processes to sense whatever sounds he or she is able to sense with these processes. That is to say, the present invention does not invade the patient's inner ear to the extent that would prevent the inner ear from functioning as best as it is able. This is in contrast to existing invasive cochlear stimulation systems, which require that an electrode be inserted directly into one of the ducts of the cochlea, usually the scala tympani. Disadvantageously, such electrode insertion may (and usually does) cause irreversible damage to that portion of the cochlea, i.e., prevents that portion of the cochlea from ever performing its normal function again, e.g., because the fluid is no longer present in the cochlea and/or because ossification occurs within that portion of the cochlea. (Of course, the benefit is that, for the typical patient who needs a cochlear implant system, the patient is able to hear, whereas prior to the implantation of the cochlear system the patient could not hear, and that portion of the cochlea where the electrode array is inserted did not perform its normal function anyway.) But, for the patient who has not lost all of the function of the cochlea, i.e., for the patient who can still hear middle and lower frequency sounds using the normal processes of the inner ear, it is desirable that an electrode be inserted into the cochlea using a process that is minimally invasive, thereby allowing the normal hearing processes of the inner ear to continue. As indicated, the present invention advantageously allows these normal hearing processes to continue, while still providing the benefits of cochlear stimulation for higher frequency sounds.

Figure 2:
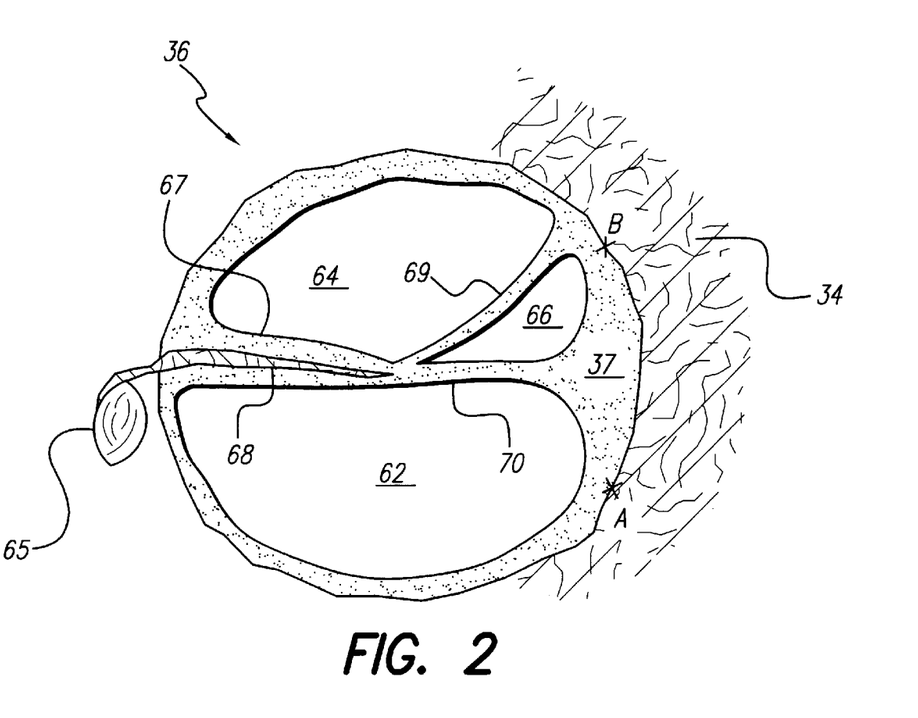
FIG. 2 illustrates a cross-sectional view of the cochlea, showing the three ducts therein, near the region where the blade electrode of the present invention is to be inserted.

Turning next to FIG. 2, a cross-sectional view of the cochlea 36 is illustrated. As seen in FIG. 2, the cochlea 36 includes three parallel ducts or channels: the scala tympani 62, the scala vestibuli 64, and the cochlear duct 66. Cochlear bony tissue 34 resides on one side, the lateral side (the right side as drawn in FIG. 2), of the cochlea 36. Spiral ganglion cells 65 reside on the other side, the medial side (the left side as drawn in FIG. 2), of the cochlea 36. Separating the three ducts are various membranes and other tissue. The Ossicous spiral lamina 67 separates the scala vestibuli 64 from the scala tympani 62. Near the lateral side, which is where the cochlear duct 66 is located, the basilar membrane 70 separates the scala tympani 62 from the cochlear duct 66; and the Vestibular (Reissner's) membrane 69 separates the scala vestibuli 64 from the cochlear duct 66. Many of the hair cells that are vibrated by fluid motion within the cochlea are located in or near the basilar membrane 70 and vestibular membrane 69. Nerve fibers 68, embedded within the spiral lamina 67 connect the hair cells with the spiral ganglion cells 65.

Still with reference to FIG. 2, it is seen that the spiral ligament membrane 37 is located between the lateral side of the spiral tympani 62 and the cochlear bony tissue 34, and between the lateral side of the cochlear duct 66 and the bony tissue 34. The spiral ligament 37 also typically extends around at least a portion of the lateral side of the scala vestibuli 64 and the cochlear bony tissue 34. As will be explained more fully below, the present invention teaches separating, or delaminating, the spiral ligament 37 from the cochlear bony tissue 34 between the points "A" and "B". Such delamination or separation creates a pocket 39, best seen in FIG. 6, into which the blade electrode 52 of the present invention may be inserted.

Figures 3A, 3B:
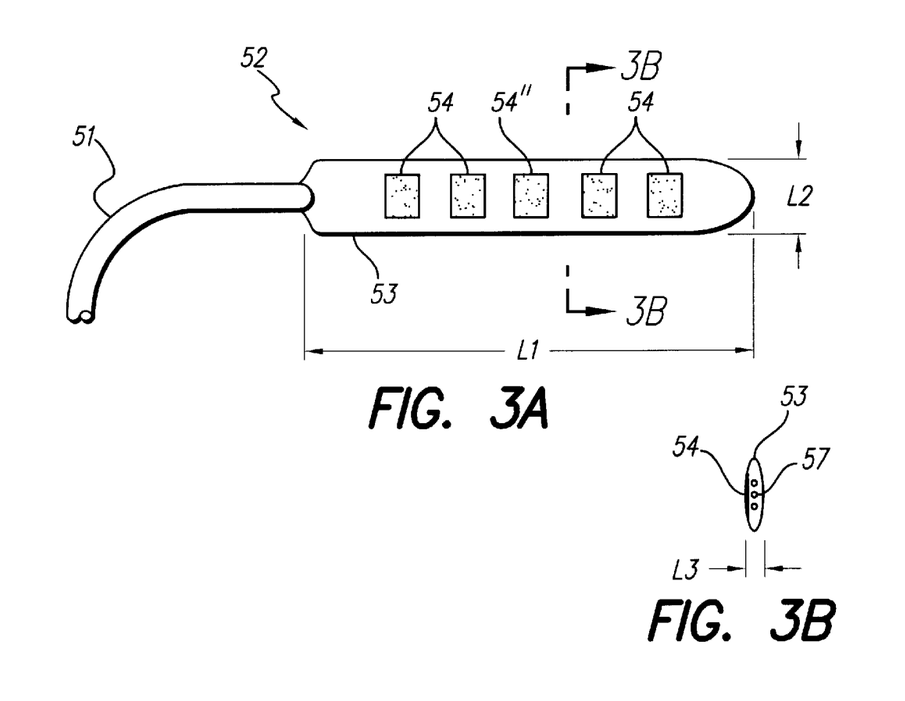
FIGS. 3A and 3B illustrate one embodiment of a blade electrode made in accordance with the present invention.

Turning next to FIGS. 3A and 3B, a blade electrode array 52 made in accordance with one embodiment of the invention is illustrated. FIG. 3A depicts a front view of such electrode array 52 and FIG. 3B depicts a side view. The blade electrode array 52 includes a plurality of spaced-apart electrode contacts 54 that are carried on a suitable flexible carrier 53. Each electrode contact 54 is electrically connected to at least one wire 57 that is embedded within the flexible carrier 53, and within the lead 51. It is through these wires 57 that the ICS 50 (FIG. 1) provides electrical stimuli to selected ones of the electrode contacts 54. A mechanical or other transducer 54" may also be included on the electrode array in some embodiments, as described below. Such transducer 54" is not required, but is only optional.

As is evident from FIGS. 3A and 3B, the flexible carrier is flat and thin, like a blade, with the electrode contacts 54 all residing along one surface, e.g., the medial surface (the surface which faces the medial wall of the cochlea when the array is inserted into the cochlea), of the flat portion of the blade. Such configuration is only exemplary, however, and it is to be understood that the electrode contacts may reside on both flat surfaces of the flexible carrier, or they may be bands that encircle the flexible carrier.

In one embodiment, the electrode array 52 has a length L1 of about 10 mm, and has a width L2 of about 1.2 mm, and has a thickness L3 of about 0.2 mm. These dimensions are only exemplary, and the actual dimensions may vary as needed. In particular, the length of the array 52 may vary from as short as about 4 mm to as long as about 30 mm, and the number of electrode contacts may vary from as few as one or two to as many as twenty-four or more.

A preferred manner of making the electrode array 52 having all of its electrode contacts on a medial side of the carrier, and having individual wires connected to each of the electrode contacts, is disclosed in U.S. Pat. No. 6,129,753, which patent is incorporated herein by reference. It is to be emphasized that the method disclosed in the '753 patent of making the electrode array is not the only way an electrode array 52 could be made. However, it represents an easy and inexpensive (and thus a preferred) way to make the electrode array.

The preferred method of making the electrode array 52, described in the referenced '753 patent, is based on the principle of attaching (by the process of resistance welding) electrode contacts made from precious, biocompatible material (such as platinum or its alloys) to a foil carrier made from a non-toxic but chemically-active metal, such as iron (Fe). Resistance welding advantageously provides a secure attachment of the electrode material to the foil carrier without causing a deep fusion of the two materials being attached. The resulting shallow fusion contact, in turn, allows clean exposed electrode surface areas to be formed when the foil carrier is eventually chemically etched away. Other types of attachment that result in shallow fusion of the electrode material and the foil carrier sheet material may also be used in lieu of resistance welding. Once attached to the metal carrier, the electrode contacts remain in a desired and stable position allowing easy connecting of a wiring system and subsequent molding of the polymer carrier. After completion of the molding process, the metal foil carrier is chemically etched away using a mixture of diluted acids, such as $HNO_3$ and HCl. The precious metal contacts and polymer are immune to the acid and remain in their intact, unaltered shape, and thereby provide the desired electrode array structure.

Figure 4:
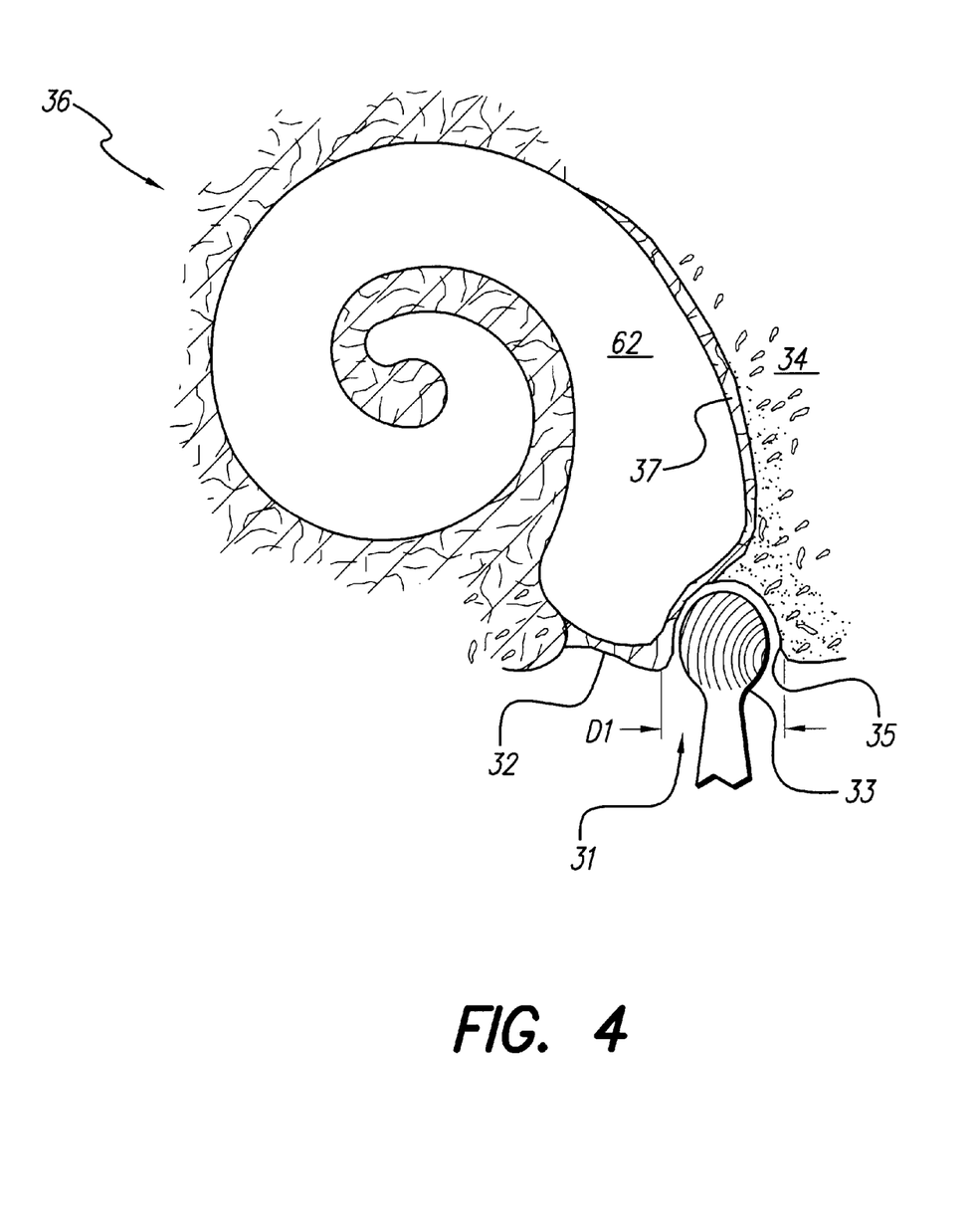
FIG. 4 illustrates a first step of inserting a blade electrode in accordance with the invention, which step involves drilling a "soft cochleostomy" about 1 mm in diameter just to the side of the round window, but without penetrating the spiral ligament membrane.

Next, with reference to FIG. 4, the preferred process for making a soft cochleostomy 31 for use by the invention is illustrated. FIG. 4 illustrates the spiraling scala tympani 62 of the cochlea 36. The round window membrane 32, inter alia, retains the fluid held within the scala tympani 62 of the cochlea from escaping into the middle ear. The cochlea 36, especially the basal region of the cochlea in the vicinity of the round window 32, is surrounded by bony tissue 34. As seen in FIG. 4, a first step for making a suitable soft cochleostomy 31 is to drill a hole 35 having a diameter D1 of about 1.0 mm in diameter, on a lateral side of the round window 32, using a suitable drilling or grinding tool 33. A preferred location for the drilled hole 35 is about 1 mm from the closest edge of the round window 32, but any suitable location may be used. The hole 35 is drilled as deep as possible without penetrating the spiral ligament membrane 37. A skilled surgeon is able to recognize when this depth has been reached by the change of color of the bottom of the hole 35 when only the spiral ligament membrane 37 remains.

Figure 5:
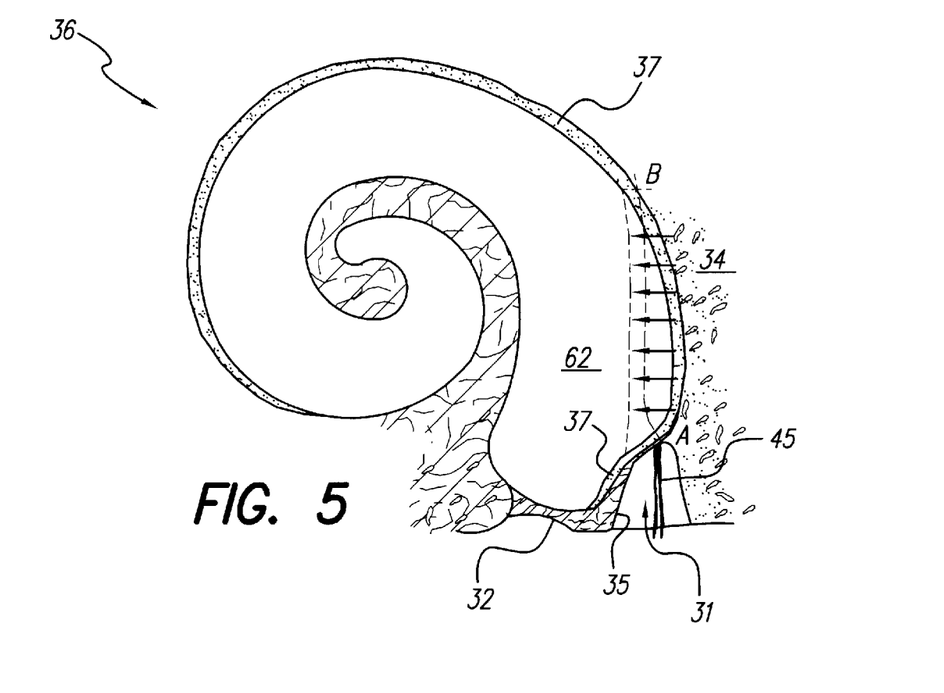
FIG. 5 illustrates a second step of inserting an electrode in accordance with the invention, which second step involves using a bladed instrument to force the spiral ligament away from the cochlear bone along the lateral wall of the cochlea.

Next, as seen in FIG. 5, a micro-spear 45, and/or micro-pick, or equivalent probe tool, is used to delaminate, i.e., separate, the spiral ligament membrane 37 from the cochlear bony tissue 34. That is, as shown in FIG. 5, the tip of the micro-spear 45 is carefully pressed against the spiral ligament membrane 37 at the bottom of the hole 35 so as to push it away from the cochlear bone tissue 34, but without punching a hole through the spiral ligament membrane. As a first section of the spiral ligament membrane 37 is pushed away from the bone tissue 34, the micro-spear 45 is inserted into the space created by the delamination or separation to delaminate or separate additional spiral ligament membrane 37 from the bone tissue 34. This process continues until all of the spiral ligament membrane 37 between points "A" and "B" has been separated from the bone tissue 34, thereby creating a pocket 39 between the lateral side of the spiral ligament membrane 37 and the medial side of the bone tissue 34, as shown in FIG. 6.

Figure 6:
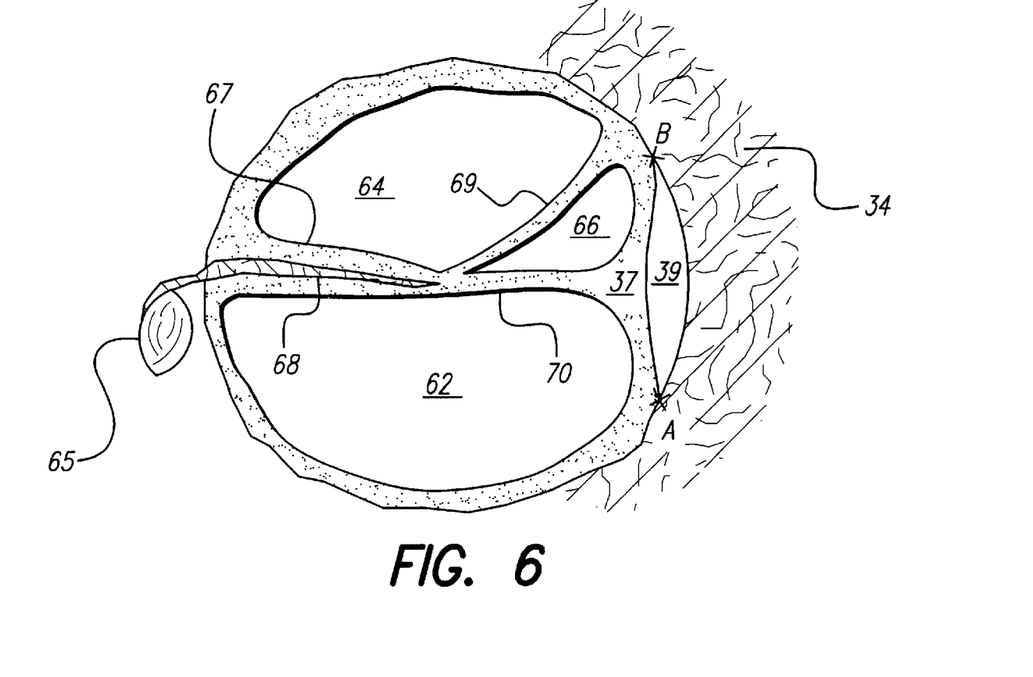
FIG. 6 illustrates the pocket that is created behind the spiral ligament after the second step of the insertion method is carried out.
Figures 7, 8, 9:
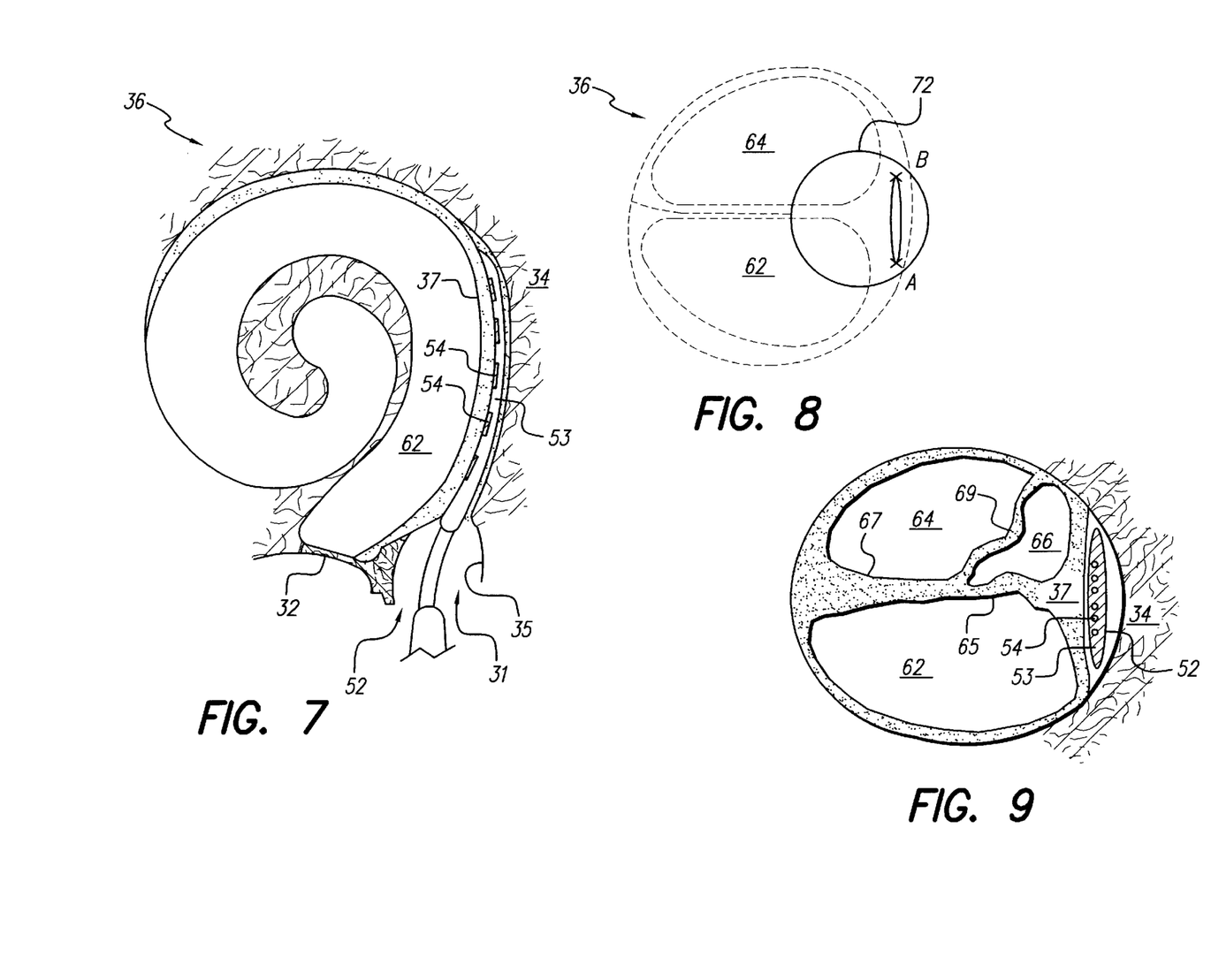
FIG. 7 illustrates a third step of inserting an electrode in accordance with the invention, which third step involves inserting the bladed electrode into the pocket space made behind the spiral ligament.
FIG. 8 schematically depicts the general area, in cross section, where the influence of the electrical stimuli provided through the electrode of the present invention is predominately felt.
FIG. 9 shows a cross-sectional representation of the cochlea after the electrode of the present invention has been inserted behind the spiral ligament membrane.

Once the delamination of the spiral ligament membrane 37 from the bony tissue 34 has been accomplished, so as to create the pocket 39, as seen in FIG. 6, the blade electrode array 52 is inserted into the pocket 39, as shown in FIG. 7, so that the electrode contacts 54 face the medial side of the cochlea. When fully inserted, each of the electrode contacts 54 are in contact with the delaminated surface of the spiral ligament membrane 37.

With the electrode array 52 inserted as shown in FIG. 7, the electrode contacts 54 are positioned to apply an electrical stimulus that is felt and most effective at stimulating nerves and cells within the circled region 72 shown in FIG. 8. Such circled region advantageously includes most of the hair cells and the nerve fibers that attach to such hair cells, and which in turn connect with the spiral ganglion cells 65.

FIG. 9 shows in cross section the electrode array 52 when inserted between the spiral ligament membrane 37 and the cochlear bony tissue 34 in accordance with the present invention. As seen in FIG. 9, the insertion of the electrode array 52 in the manner described is minimally invasive. That is, the scala tympani 62 and the scala vestibuli 64 remain essentially undisturbed by the presence of the electrode 52. Only the cochlear duct 66 may be distorted somewhat when viewed in cross section, by the presence of the electrode array 52, and such distortion does not prevent the scala tympani 62 and the scala vestibuli 64 from performing their basic function. Hence, the patient is able to sense sounds through the normal hearing processes that occur within the inner ear to the same degree as he or she could do so before the implant of the electrode array 52. Advantageously, however, the electrode array 52, and the ICS 50 to which it is connected, and related components, may be used to assist the patient with hearing higher frequency sounds that he or she was previously unable to hear, or to reduce tinnitus (a condition which plagues some patients even though they experience normal hearing).

Figure 10:
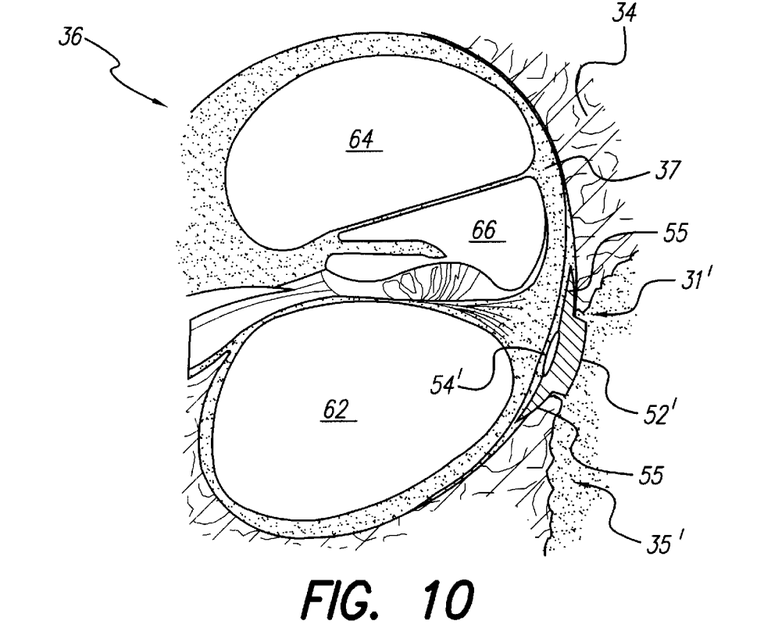
FIG. 10 shows a sectional view of the cochlea, depicting the three channels therein, and further depicting a blade electrode array having side fins, in accordance with an alternative embodiment of the invention, positioned under soft tissue of the lateral wall of the cochlea.

Turning next to FIG. 10, a cross-sectional view of the cochlea 36 is illustrated. The view of the cochlea shown in FIG. 10 is similar to the view shown in FIG. 2, and the same or similar reference numerals are used to denote like parts as are used in connection with FIG. 2.

As seen in FIG. 10, a hole 35' is drilled in the bony tissue 34 near the side of the cochlea 36. Such hole 35', which may be drilled as a slot, as shown best in FIG. 13, allows a soft cochleostomy 31' to be made that allows access into the space between the spiral ligament 37 and the bony tissue 34. A blade electrode array 52' having side fins 55 made in accordance with an alternative embodiment of the invention is inserted into the slot hole 35', with the side fins 55 being slid or positioned into the space between the spiral ligament 37 and the bony tissue 34, thereby holding electrode contacts 54', along one side of the blade electrode array 52', so as to face the cochlea 36.

Figure 11:
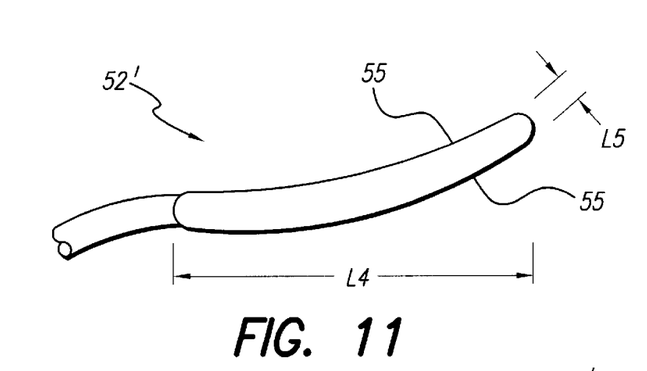
FIG. 11 illustrates a top view of the electrode portion of the alternative blade electrode array with side fins shown in FIG. 10, and further illustrates that the electrode array portion has a length L4 (which is preferably about 10 mm) and a length L5 (which is preferably about 3 mm)
Figure 12:
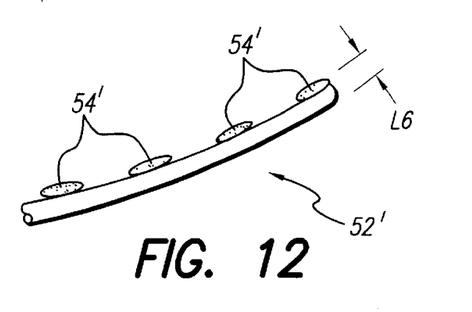
FIG. 12 illustrates a side view of the alternative blade electrode array with side fins shown in FIG. 10, and further illustrates that the electrode array portion has a thickness L6 (which is preferably about 1 mm)

FIGS. 11 and 12 show top and side views, respectively, of the blade portion of the electrode array 52'. As seen best in FIG. 11, side fins 55 extend away from opposite sides of the array. The length of the blade portion is a distance L4, which is preferably about 10 mm. The width of the array is a distance L5, which is preferably about 3 mm, and the thickness is a distance L6, which is preferably about 1 mm. As seen best in FIG. 12, the electrode contacts 54' are spaced apart along one edge of the blade electrode 52'. This edge (the edge on which the electrode contacts 54' are located) is the side of the electrode array 52' that faces towards the cochlea when the blade electrode is placed within the soft cochleostomy 31'.

Figure 13:
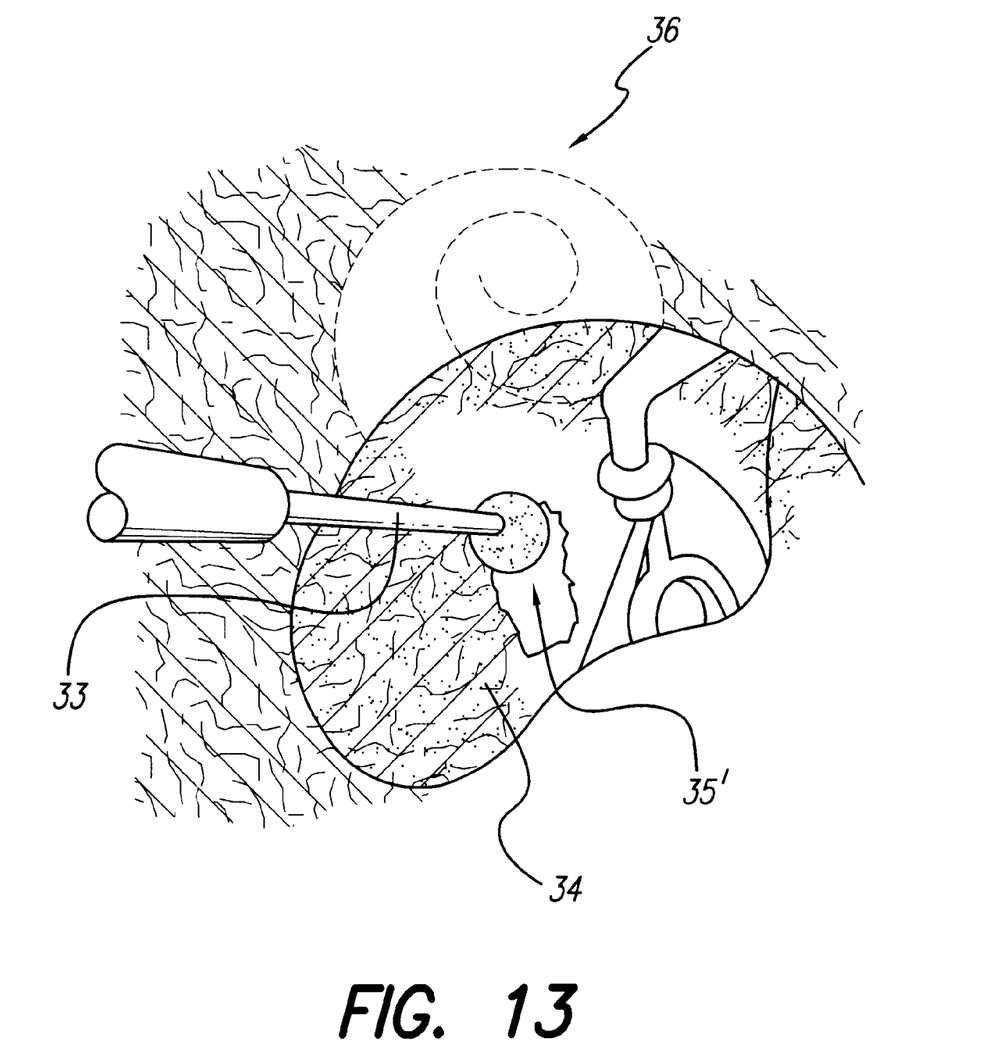
FIG. 13 illustrates the manner in which a soft cochleostomy is made in order to insert the alternative blade electrode array embodiment of FIG. 10, where such cochleostomy is positioned somewhat more on the side of the cochlea so as to allow the fins of the electrode array to be slid between the tissue and bone.

FIG. 13 illustrates the use of a drilling tool 33 to create a slot hole 35' in the bony tissue 34 near the cochlea 36. The blade electrode array 52' may then be laid into the slot hole, with the electrode contacts 54' facing the cochlea, and with the side fins 55 being slid or positioned into the space between the spiral ligament 37 and the bony tissue 34.

As described above, it is thus seen that the present invention provides an electrode array for stimulating nerves and cells of the inner ear, e.g., the cochlea, without interfering with the normal operation of the inner ear, thereby allowing the selective activation of such electrode array to supplement the normal hearing processes that occur within the inner ear, or to treat other symptoms, such as tinnitus.

It is further seen that the invention provides a method of inserting an electrode array into the inner ear without penetrating into the scala tympani or scala vestibuli of the cochlea, thereby permitting the cochlea to perform its normal hearing function without interference.

Because the electrode array of the invention may be inserted into the inner ear in a minimally invasive manner without interfering with the normal hearing processes that occur within the cochlea, it is noted that the electrode array may also be fitted with one or more mechanical transducers, e.g., elements that convert electrical signals to mechanical energy. Such mechanical transducers may be carried on the flexible carrier 53 in place of one or more of the electrode contacts 54, e.g., the element 54" shown in FIG. 3A could be a mechanical transducer and/or a combination mechanical transducer and electrode contact. When energized, such mechanical transducers impart vibrations to the spiral ligament membrane with which they are in contact, thereby establishing waves of fluid motion within the scala tympani 62 and/or the scala vestibuli 64 and/or the cochlear duct 66 that assist or aid in the hearing process. Any suitable mechanical transducer that could be configured for being carried by the flat carrier 53 could be used for this purpose, e.g., a piezoelectric film.

It should also be noted that applying an electrical stimulus to the spiral ligament membrane 37 causes some of the tissue elements within such membrane to be excited, i.e., to depolarize and contract. Such depolarization and contraction also helps set up wave motions within the fluids contained within the cochlear duct, scala vestibuli and scala tympani. In other words, to a certain extent, the spiral ligament tends to act as its own mechanical transducer, converting the electrical impulses provided through the electrode contacts to mechanical motion that is transferred to the cochlear fluids and that aids in the hearing process.

While the invention herein disclosed has been described by means of specific embodiments and applications thereof, numerous modifications and variations could be made thereto by those skilled in the art without departing from the scope of the invention set forth in the claims.

What is claimed is:

1. A cochlear stimulation system comprising:
an electrode array comprising a flexible carrier and a plurality of spaced-apart electrode contacts carried by the flexible carrier, each electrode contact having at least one wire connected thereto through which electrical connection may be made, wherein the electrode array comprises a blade electrode array, wherein the blade electrode array defines a width (L2) and a thickness (L3) wherein the width is greater than the thickness; and
an implantable cochlear stimulator (ICS) electrically connected to the electrode array, the ICS including means for generating electrical stimuli that may be selectively applied to the electrode contacts of the electrode array in response to sensed audio sounds;
wherein the electrode array is adapted to be inserted into the inner ear of a patient in between the spiral ligament membrane and the cochlear bony tissue located along the lateral side of the cochlea.

2. The cochlear stimulation system of claim 1 further including at least one mechanical transducer that is carried on the flexible carrier and which is excitable by an applied electrical current.

3. The cochlear stimulation system of claim 1 wherein the flexible carrier further has side fins on opposing sides thereof, wherein the side fins and flexible carrier define a width (L5) and a thickness (L6) wherein the width is greater than the thickness.

4. The electrode array of claim 1 further including at least one mechanical transducer carried on the flexible carrier, wherein the mechanical transducer includes means for converting electrical energy to mechanical energy.

5. The electrode array of claim 1 wherein the flexible carrier on which the electrode contacts are carried has a length of approximately 10 mm, a width of about 1.2 mm, and a thickness of about 0.2 mm.

6. An electrode array comprising a flexible carrier and a plurality of spaced-apart electrode contacts carried along one side of the flexible carrier, each electrode contact having at least one wire connected thereto through which electrical connection may be made, the electrode array comprising a blade electrode array having side fins on opposing sides thereof, wherein the side fins and flexible carrier define a width (L5) and a thickness (L6) wherein the width is greater than the thickness; and wherein the electrode array is adapted to be inserted into the inner ear of a patient so as to lie between the spiral ligament membrane and the cochlear bony tissue located along the lateral side of the cochlea.

7. A method of inserting an electrode array into the inner ear in a minimally-invasive manner, the electrode array comprising a blade electrode that is flat in one direction and thin in another direction, the method comprising:
drilling a soft cochleostomy on the lateral side of the round window, said soft cochleostomy comprising a hole that extends only to the spiral ligament membrane without penetrating through the spiral ligament membrane;
creating a space or pocket between the spiral ligament membrane and the cochlear bony tissue; and
inserting the blade electrode into the pocket.

8. The method of claim 7 wherein creating a space or pocket between the spiral ligament membrane and the cochlear bony tissue comprises inserting a probe into the soft cochleostomy and thereafter using the probe to separate or delaminate the spiral ligament membrane from the cochlear bony tissue to which the spiral ligament membrane is attached.

9. The method of claim 7 wherein the electrode array has a plurality of spaced-apart electrode contacts along one surface thereof, and wherein the method further comprises inserting the blade electrode into the pocket so that all of the electrode contacts face the spiral ligament membrane.

10. The method of claim 7 wherein the electrode array has at least one mechanical transducer positioned on one surface thereof, and wherein the method further comprises inserting the blade electrode into the pocket so that the at least one mechanical transducer faces and contacts the spiral ligament membrane.

11. The method of claim 7 wherein drilling a soft cochleostomy comprises drilling a hole having a diameter of about 1 mm on the lateral side of the round window membrane.

12. A method for stimulating nerves and cells of the inner ear without interfering with the normal operation of the inner ear, thereby allowing the selective activation of said electrode array to supplement the normal hearing processes that occur within the inner ear, or to treat other symptoms, such as tinnitus, the method comprising
inserting an electrode array into the inner ear between a spiral ligament membrane and cochlear bony tissue without penetrating into the scala tympani or scala vestibuli of the cochlea, said electrode array having a plurality of spaced-apart electrode contacts thereon; and
selectively electrically activating the electrode contacts.

13. The method of claim 12 wherein inserting an electrode array into the inner ear between the spiral ligament membrane and cochlear bony tissue without penetrating into the scala tympani or scala vestibuli of the cochlea comprises:
drilling a soft cochleostomy on a lateral side of the round window of the inner ear, said soft cochleostomy comprising a hole that extends only to the spiral ligament membrane without penetrating through the spiral ligament membrane;
creating a space or pocket between the spiral ligament membrane and the cochlear bony tissue; and
inserting the blade electrode into the pocket.

14. The method of claim 13 wherein creating a space or pocket between the spiral ligament membrane and the cochlear bony tissue comprises inserting a probe into the soft cochleostomy and thereafter using the probe to delaminate the spiral ligament membrane from the cochlear bony tissue to which the spiral ligament membrane is attached.

* * * * *